United States Patent
Chow

(10) Patent No.: US 9,023,381 B2
(45) Date of Patent: May 5, 2015

(54) ENHANCED MEDICINAL DELIVERY SYSTEM PROCESSES AND PRODUCTS THEREBY ESPECIALLY USEFUL FOR CHILDREN

(76) Inventor: Michelle Chow, Irvine, CA (US)

( * ) Notice: Subject to any disclaimer, the term of this patent is extended or adjusted under 35 U.S.C. 154(b) by 638 days.

(21) Appl. No.: 11/933,003

(22) Filed: Oct. 31, 2007

(65) Prior Publication Data

US 2008/0181934 A1    Jul. 31, 2008

Related U.S. Application Data

(60) Provisional application No. 60/886,913, filed on Jan. 26, 2007.

(51) Int. Cl.
*A61K 9/68* (2006.01)
*A61K 47/00* (2006.01)
*A61K 9/00* (2006.01)
*A61K 9/16* (2006.01)

(52) U.S. Cl.
CPC ............. *A61K 9/0056* (2013.01); *A61K 9/1623* (2013.01); *A61K 9/1652* (2013.01); *A61K 9/1658* (2013.01)

(58) Field of Classification Search
None
See application file for complete search history.

(56) References Cited

U.S. PATENT DOCUMENTS

| | | | |
|---|---|---|---|
| 5,386,909 A * | 2/1995 | Spector | 206/457 |
| 5,431,915 A | 7/1995 | Harvey et al. | |
| 6,165,531 A * | 12/2000 | Harding et al. | 426/512 |
| 6,365,209 B2 | 4/2002 | Cherukuri | |
| 6,432,442 B1 * | 8/2002 | Buehler et al. | 424/441 |
| 6,521,257 B1 | 2/2003 | Taniguchi et al. | |
| 6,689,386 B2 | 2/2004 | Baichwal | |
| 7,067,150 B2 | 6/2006 | Farber et al. | |
| 2004/0001873 A1 | 1/2004 | Base et al. | |
| 2004/0013783 A1 * | 1/2004 | Miller | 426/575 |
| 2004/0265359 A1 | 12/2004 | Sacks et al. | |
| 2005/0045197 A1 | 3/2005 | Gelder | |

* cited by examiner

*Primary Examiner* — Scott Long
*Assistant Examiner* — Lyndsey Beckhardt
(74) *Attorney, Agent, or Firm* — Brown Rudnick, LLP; Daniel A. Palmer; Peter Jon Gluck

(57) ABSTRACT

Pharmacologically effective amounts of a medication are delivered in pleasant tasting delivery vehicles, including gelatins and candies. Mechanisms for the reduction in surface area of noxious taste-imparting aspects of conventional medicines, and dilutive effects of positive masking elements for such medicines, especially products for inducing children to take medicines, are taught—in combination with processes and products thereby.

5 Claims, No Drawings

ENHANCED MEDICINAL DELIVERY SYSTEM PROCESSES AND PRODUCTS THEREBY ESPECIALLY USEFUL FOR CHILDREN

CROSS REFERENCE TO RELATED APPLICATIONS

This disclosure claims full Paris Convention priority and all related priority rights from U.S. Provisional Patent Application Ser. No. 60/886,913 filed 26 Jan. 2007, in the name of the present inventor et seq. Said application is expressly incorporated by reference as if expressly set forth herein.

BACKGROUND OF THE DISCLOSURE

The present disclosure relates to novel enhanced drug delivery systems, processes and products thereby. The present disclosure particularly relates to mechanisms for the reduction in surface area of noxious taste-imparting aspects of conventional medicines, and dilutive effects of positive masking elements for such medicines in addition to novel and unexpected inherently related aspects of these ways to preclude the amount of time such mechanisms impact children's taste-buds, especially products for inducing children to take medicines.

SUMMARY OF THE DISCLOSURE

Briefly stated, pharmacologically effective amounts of a medication are delivered in pleasant tasting delivery vehicles, including, but not limited to agar agar, gelatins and candies. Mechanisms for the reduction in surface area of noxious taste-imparting aspects of conventional medicines, and dilutive effects of positive masking elements for such medicines, especially products for inducing children to take medicines, are taught—in combination with processes and products thereby.

Pharmacologically effective amounts of a medication are delivered in any number of variable pleasant tasting delivery vehicles, including, but not limited to agar agar, gelatins and candies. Each of the alternate variable pleasant tasting delivery vehicles likewise are packaged to be assembled and dispensed by a parent, professional health-care provider, elder sibling or other competent day-care provider, including au-pairs and nannies. Children, who otherwise would be unwilling to take their medicine, will consume the medication contained in the delivery vehicles more readily than with traditional delivery vehicles.

According to embodiments of the present disclosure, there is disclosed a method comprising masking the flavor of a therapeutic agent by incorporating the drug into a delivery vehicle that children will readily consume, and delivering a pharmacologically effective dose of a drug by feeding a dose of the delivery vehicle containing the drug to a child.

According to embodiments of the present disclosure, a composition is disclosed comprising a therapeutic agent and a flavored delivery vehicle that children will readily consume.

According to embodiments of the present disclosure, a process for providing a pharmacologically effective dose of an oral therapeutic agent in a delivery vehicle further comprising a packetized system to be fed to children.

According to embodiments of the present disclosure, there is provided a process for making a palatable medicinal product having reduced surface area noxious taste impacting aspects of admixing a therapeutically effective dosage of a drug with agar and at least a sweetened mixture.

According to embodiments of the present disclosure, there is disclosed a process which combines a therapeutically effective drug with agar and at least a sweetened mixture with water and boiling the mixture.

According to embodiments of the present disclosure, there is disclosed a process with a therapeutically effective drug with agar and at least a sweetened mixture whereby optionally adding a coloring agent and then dividing the resultant slurry into aliquots while shaking the slurry mixture, whereby cooling the end product and finishing the formulation are further taught.

According to embodiments of the present disclosure there is provided a kit comprising in combination a Jell-I Dose™ assembly comprised of at least a therapeutic agent, along with a pre-curser constituent elements to a flavored delivery vehicle and instructions for formulating and mixing them.

DETAILED DESCRIPTION OF THE DISCLOSURE

The present inventor has discovered how to provide medicines to children. U.S. Provisional Patent Application Ser. No. 60/886,913 filed 26 Jan. 2007, in the name of the present inventor, is expressly incorporated by reference as if expressly set forth herein. Likewise expressly incorporated are U.S. Pat. Nos. 6,521,257; 6,689,386; 6,432,447; 6,365,209; and 7,067,150, as fully set forth herein.

Children often resist taking medications due to undesirable flavors of the medication and delivery vehicles. Even medications that are designed specifically for children fail to fully mask the flavors of the medications contained therein, and children quickly learn to resist taking even these formulations. The instant teachings overcome these longstanding issues, using agar agar among other things.

The present inventors have discovered that by putting therapeutic agents into delivery vehicles such as gelatin based products, candy, or popsicles, children are more likely to take the medication, and may not even know they are taking the medication.

Mechanisms of action for the instant disclosure include both several log reduction to the surface area that contains molecules of drugs that come in contact with taste-buds to the surface area being devoid of the noxious tasting medicine's dilutive effects of positive masking elements, the dilutive effect of larger volume of delivery vehicle, (e.g., agar agar) to deliver the same amount of medicine, encapsulation, taste and texture, and minimize taste-bud contacting time. Both of these approaches improve over tablets and capsules, the current state-of-the-art, or standard of care.

The consumption of powders suffers from problems such as low solubility or dispersability in water or juice and unpleasant mouth feel and taste. Many agents are poorly absorbed into the body and a common approach to this problem is to consume larger doses, which can result in unpleasant side effects including cramping, bloating and flatulence. Thus, a number of different delivery systems have been developed to attempt to improve oral methods of delivering various supplements or active ingredients. However, these are overwhelming rejected by children, and often senior citizens.

In contradistinction to the present disclosure, a number of encapsulated formulations have been developed which encapsulate or retain functional ingredients in various glassy, sintered or chewy confectionery-type matrixes. These capsules are not generally well tolerated by children, the elderly or anyone compelled to consume them daily. The teachings of the instant disclosure, however, leverage positive aspects of the mechanism without triggering a gag-reflex. In general, the confectionery serves as a solid continuous matrix for the active ingredient or supplement. The active ingredient is delivered according to the dissolution rate of the confectionery matrix, which confers a solid taste in the mouth. Crushing the confectionery is a solution for the consumer to speed up the release of the active ingredient but this solution may be undesirable as dental problems may arise and/or the release rate of the active ingredient incorporated therein may no longer be optimal. Depending upon the method of manufacturing the confectionery matrix, the active ingredient may suffer from deterioration or damage due to heat and/or mechanical stresses in the manufacturing process.

Often, high deterioration rates due to strong processing conditions are compensated for by overdosing of the active ingredient in the confectionery matrix, however, this is a costly method resulting in the wastage of a lot of the active ingredient. The "solid" taste a pressed tablet or glassy matrix may provide in the mouth may also be considered as not very attractive in the context of delivering active ingredients, especially if the product is supposed to be primarily a confectionery. Unlike the teachings of the present disclosure, tolerance by children and compliance with medical instructions is lower.

Similarly, Liquid-filled boiled sweets are known and may also be used to deliver active ingredients. However, despite the fact the centre is primarily liquid, the whole product has a tendency to melt as one piece in the mouth. The liquid center does not release from the casing rapidly but rather melts slowly and progressively, thus making a pasty mass. Once again, packets of the instant disclosure improves this type of approach, especially with children.

Powdered sugar filling in a high boiled sweet has also been known for many years in the manufacture of traditional confectioneries such as "Sherbet Lemon" in England. This type of confectionery behaves in the mouth in a way similar to liquid-filled boiled sweets with the casing and filling melting slowly in the mouth and has not been used for delivering active ingredients. Each of these prior art methods has been overcome by the instant teachings.

It has been known in the art of food stuff, confectionery and chewing gum preparation to provide protection to the active ingredients by the use of similarly motivated, yet alarmingly less effective protection systems, including providing a protective coating around the active ingredient or encapsulating the active ingredient. Such protective systems have been employed for various reasons, such as for protection of the active ingredient, both while on the shelf and during use, and for prolonged release in the oral cavity. No teaching bridging the gap and making children able to take medicine has been uncovered.

It is known in the art to protect active ingredients by encapsulating the active ingredient prior to introducing the ingredient into a final product. Some of the major classifications of encapsulation technology include liquid suspending media (water-in-oil emulsions and oil-in-water emulsions), interfacial and in situ polymerization, solvent evaporation from emulsions, desolvation, complex coacervation, polymer and polymer incompatibility, gelation, and pressure extrusion. One of skill in the art will be familiar with each of these classifications, and why a more direct solution works better.

An anion-exchange resin such as cholestyramine and a cation-exchange resin such as calcium polystyrene sulfonate or sodium polystyrene sulfonate can optionally be employed in the present invention as a specific agent in a vehicle for adsorption. Furthermore, the type of gelling agent is not particularly limited. For example, pectin, agar, arabic gum, xanthum gum, tragacanth gum, karaya gum, ghatti gum, guar gum, gellan gum, locust bean gum, alginic acid or its salt (e.g., sodiumalginate), carrageenan, gelatin, dextrin, starches (corn starch, rice starch, wheat starch, potato starch, pueraria starch, tapioca starch, carboxymethyl starch, hydroxypropyl starch, hydroxyethyl starch, chemically cross-linked starch, alpha-starch, and so on), celluloses (hydroxypropylmethyl cellulose, carboxymethyl cellulose, methyl cellulose, methylethyl cellulose, hydroxypropyl cellulose, crystalline cellulose and so on), polyvinyl alcohol, polyvinylpyrrolidone, polyethylene glycol(macrogol), or mannans can be used singly or in an appropriate combination.

Embodiments of this invention may further contain, as needed, a stabilizer, surfactant, solubilizer, buffer, sweetener, seasoning, suspending agent, coating, flavor/spice (aromatic), colorant, pH adjuster, viscosity increasing agent, Ca-supplier, dispersant, antiseptic (preservative), solvent (dissolving agent) and the like. For example, sodium alginate, various gums, glycerin, etc. can be used as a stabilizer; sodium lauryl sulfate, polysorbate 80, or the like can be used as a surfactant; ethanol or the like can be used as a solubilizer; phosphate, carbonate, and so on can be used as a buffer; purified sucrose, aspartame, fructose, sorbitol, xylitol, glucose, mannitol, maltose, trehalose, palatinose, powdered-reduced maltose millet jelly, oligosaccharide, erythritol, stevioside, glycyrrhizin, etc. can be used as a sweetener; menthol, edible fruit juice, caramel, or glucono-(-lactone, etc. can be used as a seasoning; sodium alginate, arabic gum, lactose, or the like can be used as a suspending agent; purified shellac, hydroxypropylmethyl cellulose phthalate, or the like can be used as a coating; fruit flavor, prune, mint oil, and so on can be used as a flavor/spice (aromatic); orange essence, edible dye, caramel, or the like can be used as a colorant; citric acid or its salt, tartaric acid or its salt, succinic acid, lactic acid, calcium lactate, phosphate, glucono-.delta.-lactone, etc. can be used as a pH adjuster; dextrin, xanthum gum, soybean lecithin, polyethylene glycol, etc. can be used as a viscosity increasing agent; calcium lactate, calcium hydrogenphosphate, calcium carbonate, calcium chloride, calcium citrate, calcium sulfate, etc. can be used as a Ca-supplier; arabic gum, starches, crystalline cellulose, lactose, etc. can be used as a dispersant; sorbic acid or its salt, benzoic acid or its salt, p-oxybenzoates, or the like can be used as an antiseptic (preservative); and purified water or ethanol, or the like can be used as a solvent (dissolving agent).

Early iteration of the present disclosure (the Jell-I Dose™ brand of delivery system, available from Michelle Chow, Irvine, Calif.). An example of a high dose, insoluble drug is ibuprofen, which is a non-steroidal anti-inflammatory agent ("NSAID"). Several immediate release forms of ibuprofen are commercially available, e.g., Motrin™ (available from Upjohn) and Brufen™ (available from The Boots Company PLC), and a sustained release ibuprofen formulation, Brufen Retard™, is commercially available from the Boots Company PLC Indomethacin, another high dose insoluble NSAID, is commercially available in sustained release form as Indocin™ from Merck & Co., Inc.

The formulations of the present invention may optionally also include an inert diluent. Any generally accepted soluble or insoluble inert diluent material can be used. Preferably, the inert diluent comprises a monosaccharide, a disaccharide, a polyhydric alcohol, a cellulose (such as microcrystalline cellulose), starches, and/or mixtures thereof. Examples of suitable inert pharmaceutical fillers include sucrose, dextrose, lactose, microcrystalline cellulose, xylitol, fructose, sorbitol, mixtures thereof and the like. However, it is known that a soluble pharmaceutical filler such as dextrose, sucrose, or mixtures thereof be used.

Examples of such pre-manufactured direct compression excipients include Emcocel™ (microcrystalline cellulose, N.F.), Emdex™ (dextrates, N.F.), and Tab-Fine™ (a number of direct-compression sugars including sucrose, fructose, and dextrose), all of which are commercially available from Edward Mendell Co., Inc., Patterson, N.Y.). Other direct compression diluents include Anhydrous lactose (Lactose N.F., anhydrous direct tableting) from Sheffield Chemical, Union, N.J. 07083; Elcem™ G-250 (Powdered cellulose, N.F.) from Degussa, D-600 Frankfurt (Main) Germany; Fast-Flo Lactose™ (Lactose, N.F., spray dried) from Foremost Whey Products, Banaboo, Wis. 53913; Maltrin™ (Agglomerated maltrodextrin) from Grain Processing Corp., Muscatine, Iowa 52761; Neosorb 60™ (Sorbitol, N.F., direct-compression) from Roquette Corp., 645 5th Ave., New York, N.Y. 10022; Nu-Tab™ (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel™ (Sodium starch glycolate, N.F., carboxymethyl starch) from Generichem Corp., Little Falls, N.J. 07424; Solka Floc™ (Cellulose floc) from Edward Mendell Co., Carmel, N.Y. 10512; Spray-dried lactoses (Lactose N.F., spray dried) from Foremost Whey Products, Baraboo, Wis. 53913 and DMV Corp., Vehgel, Holland; and Sta-Rx 1500™ (Starch 1500) (Pregelatinized starch, N.F., compressible) from Colorcon, Inc., West Point, Pa. 19486. Pre-manufactured directed compression excipients may also comprise all or a portion of the inert diluent.

In further embodiments of the invention, a therapeutically active agent can be incorporated (admixed, granulated, etc.) with any of the ingredients of the sustained release excipient, if so desired. The remaining formulation steps would remain essentially the same as would be understood by one skilled in the art.

According to embodiments, a therapeutic agent is incorporated into a gelatin, candy, or sugar and given to a child to eat when a dose of medicine is needed. According to embodiments, the therapeutic agent is more diluted than in traditional children's delivery methods. However, children are more likely to consume the entire delivery vehicle, thereby receiving a full dose. Additionally, for certain agents, the child is also consuming food materials that will reduce stomach irritation that is often a side effect of many therapeutic agents. Finally, children are less likely to spit out therapeutic agents delivered in this way, which ensure that a full dose is administered.

According to an embodiment, a single serve packet of colored gelatin provides a single aliquot (Jell-I Dose™) to a child, for example 50 mg of Ibuprofen. Depending on the child's weight and age, a variable number of Jell-I Dose packets will be given to the child by a responsible party. The child then is encouraged to eat each Jell-I Dose™, as a "treat" for example. Responsible parties may increase interest in the child by allowing the child to choose multiple colors of Jell-I Dose™, where the child needs more than a single Jell-I Dose™.

According to representative, but not limiting embodiments, each Jell-I Dose™ is made by adding 50 mg of ibuprofen to a single serve packet. An agar/sucrose mixture 6 ounces is mixed with 6 cups of water and heated until boiling. Gelatin manufacturer directions can also be followed according to embodiments. Prior to boiling the mixture, 50 mg of liquid ibuprofen is placed into each Jell-I Dose™ packet. One drop of a variety of food colors are added to bowls, and the boiled agar/sucrose/water mixture is divided among the bowls as desired and mixed with the food coloring and mixed. Thereafter, 2.5 tsp of colored agar/sucrose/water mixture is added to each packet, which is shaken and then cooled for 2 hours to polymerize the agar. The packets are then sealed until a child is ready to consume the contents. Artisans will recognize that other therapeutic agents may be substituted for ibuprofen.

Similarly, according to embodiment, the same principles may be employed to make popsicles or candy containing the therapeutic agents. According to these embodiments, the therapeutic agent may be added to the larger batch, mixed thoroughly, and aliquoted out into individual servings. Formulation of when the therapeutic agents is added will be determined without undue experimentation based on the chemistry of the solution to which it is being added.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A method of making a palatable medicinal product comprising:
    combining 6 ounces of an agar/sucrose mixture with 6 cups of water;
    boiling the combination;
    mixing 2.5 teaspoons of the boiled combination with 50 mg of a therapeutic agent; and
    cooling the resultant slurry to polymerize the agar/sucrose, water, and therapeutic agent mixture.

2. The method of claim 1, wherein the therapeutic agent is a non-steroidal anti-inflammatory drug (NSAID).

3. The method of claim 2, wherein the NSAID is at least one drug selected from the group consisting essentially of Ibuprofen, Acetaminophen, and Naproxen.

4. The method of claim 1, further comprising packaging into packets at least a unit dose quantity of the mixture.

5. The method of claim 4, further comprising sealing the packets of at least a unit dose quantity of the mixture.

* * * * *